(12) United States Patent
Yoo

(10) Patent No.: US 11,484,259 B2
(45) Date of Patent: Nov. 1, 2022

(54) BODY FAT COMBUSTION AMOUNT MEASUREMENT DEVICE

(71) Applicant: SENTECH GMI CORP., Paju-si (KR)

(72) Inventor: Do Joon Yoo, Seongnam-si (KR)

(73) Assignee: SENTECH GMI CORP., Paju-si (KR)

( * ) Notice: Subject to any disclaimer, the term of this patent is extended or adjusted under 35 U.S.C. 154(b) by 476 days.

(21) Appl. No.: 16/619,358

(22) PCT Filed: Jun. 4, 2018

(86) PCT No.: PCT/KR2018/006342
§ 371 (c)(1),
(2) Date: Dec. 4, 2019

(87) PCT Pub. No.: WO2018/225997
PCT Pub. Date: Dec. 13, 2018

(65) Prior Publication Data
US 2020/0138370 A1    May 7, 2020

(30) Foreign Application Priority Data
Jun. 7, 2017  (KR) .................. 10-2017-0070640

(51) Int. Cl.
*A61B 5/00* (2006.01)
*A61B 5/083* (2006.01)
*G01N 33/497* (2006.01)

(52) U.S. Cl.
CPC .......... *A61B 5/4872* (2013.01); *A61B 5/0093* (2013.01); *A61B 5/083* (2013.01);
(Continued)

(58) Field of Classification Search
CPC ....... A61B 5/0093; A61B 5/082; A61B 5/083; A61B 5/097; A61B 5/4872;
(Continued)

(56) References Cited

U.S. PATENT DOCUMENTS

| 4,970,172 A | 11/1990 | Kundu |
| 7,790,467 B1 | 9/2010 | Massick |

(Continued)

FOREIGN PATENT DOCUMENTS

| JP | 06-070932 A | 3/1994 |
| JP | 2003-079601 A | 3/2003 |

(Continued)

*Primary Examiner* — Orlando Bousono
(74) *Attorney, Agent, or Firm* — Jae Youn Kim; Novick, Kim & Lee, PLLC

(57) ABSTRACT

A body fat combustion amount measurement device includes: a sample gas passage through which an exhaled gas flows; a sample gas chamber having an inlet through which a part of the exhaled gas flowing through the sample gas passage is introduced and an outlet through which the exhaled gas is discharged, the sample gas chamber configured to define an internal space through which the exhaled gas flows; a photoionization detector disposed in the internal space of the sample gas chamber and configured to generate an electrical signal corresponding to an amount of acetone contained in the exhaled gas existing inside the sample gas chamber; and a heater configured to increase a temperature of the internal space of the sample gas chamber to prevent moisture contained in the exhaled gas from being condensed in the sample gas chamber.

10 Claims, 2 Drawing Sheets

(52) U.S. Cl.
CPC .... *G01N 33/497* (2013.01); *A61B 2562/0247* (2013.01); *G01N 2033/4975* (2013.01)

(58) Field of Classification Search
CPC ......... A61B 2562/0247; G01N 33/497; G01N 2033/4975
See application file for complete search history.

(56) References Cited

U.S. PATENT DOCUMENTS

| | | | |
|---|---|---|---|
| 8,871,521 | B2 | 10/2014 | Akers, Jr. |
| 9,089,279 | B2 | 7/2015 | Wang et al. |
| 9,456,749 | B2 | 10/2016 | Roeck et al. |
| 2003/0208133 | A1 | 11/2003 | Mault |
| 2013/0160520 | A1* | 6/2013 | Kawata ................ G01N 33/497 73/23.3 |
| 2016/0054294 | A1* | 2/2016 | Rihani ................ G01N 21/6486 73/23.3 |
| 2017/0115272 | A1* | 4/2017 | Rihani ................ G01N 33/497 |
| 2019/0120821 | A1* | 4/2019 | Atsalakis ............. A61B 5/0803 |

FOREIGN PATENT DOCUMENTS

| | | |
|---|---|---|
| JP | 2004-077467 A | 3/2004 |
| JP | 2012-118063 A | 6/2012 |
| KR | 10-2001-0044314 A | 7/2001 |
| KR | 10-2003-0009013 A | 1/2003 |

\* cited by examiner

BODY FAT COMBUSTION AMOUNT MEASUREMENT DEVICE

TECHNICAL FIELD

The present invention relates to a body fat combustion amount measurement device, and more particularly, to a body fat combustion amount measurement device capable of measuring a body fat combustion amount by detecting acetone contained in an exhaled gas of a user.

BACKGROUND ART

The source of energy used by a human body is mainly blood sugar referred to as glucose, protein or body fat. It is known that the human body primarily uses blood sugar as an energy source, then protein and finally fat. Therefore, blood sugar is usually used as a main energy source. However, body fat is used as an energy source in special situations such as diabetes, starvation due to fasting, energy consumption due to intense exercise, dietary progression through carbohydrate intake restriction, and the like.

When the human body uses body fat as an energy source, ketone bodies are produced as a product of lipolysis. The ketone bodies are a generic term for three substances, including acetoacetic acid, P-hydroxybutyric acid and acetone produced by decarbonation of these substances. The ketone bodies are produced in the liver of the human body and circulated together with the blood. It is known that a part of the ketone bodies is used as an energy source in the brain and the rest thereof is discharged as an exhaled gas through the lungs and excreted as urine.

If it is possible to detect a trace amount of ketone bodies existing in the blood, it is possible to see how much body fat is combusting. Therefore, the detection of the ketone bodies in the blood can be very useful for diet programs aimed at reducing body fat.

A urine test and a blood test are the most common methods to determine a concentration of ketone bodies in the human body.

The urine test is a method of determining a concentration of ketone bodies in the human body based on a change in the color of a test paper according to the concentration of ketone bodies contained in the urine. The urine test has an advantage in that it is a relatively simple measurement method. However, the urine test is not suitable as a means for knowing the current concentration because it is a means for telling the concentration of ketone bodies in the human body about 4 hours ago. In addition, the urine test is not suitable as a quantitative analysis method because the test results vary greatly depending on the water intake amount or the like.

The blood test can measure quantitatively the amount of ketone bodies present in the blood in a relatively accurate manner. However, it is cumbersome to collect the blood.

In addition to the ketone body concentration measurement method described above, a technique for measuring an amount of ketone bodies in the blood by analyzing an exhaled gas has been studied in recent years. Acetone contained in the exhaled gas is closely related to the amount of ketone bodies contained in the blood. Therefore, the amount of ketone bodies in the blood can be calculated by measuring the amount of acetone contained in the exhaled gas. The exhaled gas mainly contains acetone among the ketone bodies.

For example, U.S. Pat. No. 4,970,172 discloses a method for measuring an amount of acetone by causing acetone contained in an exhaled gas to react with a matrix material containing nitroprusside salts and amines. In addition, U.S. Pat. No. 8,871,521 discloses an apparatus including a container provided with a powder whose color is changed when reacted with a ketone body (mainly acetone) contained in an exhaled gas. However, these methods have a problem in that it is not possible to measure the amount of ketone bodies contained in the exhaled gas in real time.

As a method for improving this problem, U.S. Patent Application Publication No. 2003-0208133 discloses a method for measuring a metabolic rate and an amount of ketone bodies contained in an exhaled gas to estimate a body fat decomposition amount using the metabolic rate and the ketone body amount thus measured. However, the device for such a method is complicated in structure and difficult to carry.

In addition, Korean Patent Application Publication No. 10-2001-0044314 discloses a method for measuring an amount of ketone bodies contained in an exhaled gas collected by an exhaled gas collection unit using a semiconductor type ketone gas sensor. In addition, U.S. Pat. No. 9,456,749 discloses a portable electronic device for measuring a ketone body concentration using a metal oxide sensor. However, the method using the semiconductor type gas sensor has a problem that due to the poor selectivity and stability thereof, it is difficult to distinguish acetone from other components contained in an exhaled gas.

PRIOR ART DOCUMENTS

Patent Documents

Patent Document 1: U.S. Pat. No. 4,970,172
Patent Document 2: U.S. Pat. No. 8,871,521
Patent Document 3: U.S. Patent Application Publication No. 2003-0208133
Patent Document 4: Korean Patent Application Publication No. 10-2001-0044314
Patent Document 5: U.S. Pat. No. 9,456,749
Patent Document 6: U.S. Pat. No. 7,790,467
Patent Document 7: U.S. Pat. No. 9,089,279

SUMMARY

With the aforementioned problems in view, it is an object of the present invention to provide a body fat combustion amount measurement device capable of measuring an amount of acetone contained in an exhaled gas using a photoionization detector and consequently measuring a body fat combustion amount relatively quickly and accurately in real time.

According to one aspect of the present invention, there is provided a body fat combustion amount measurement device, including: a sample gas passage through which an exhaled gas flows; a sample gas chamber having an inlet through which a part of the exhaled gas flowing through the sample gas passage is introduced and an outlet through which the exhaled gas is discharged, the sample gas chamber configured to define an internal space through which the exhaled gas flows; a photoionization detector disposed in the internal space of the sample gas chamber and configured to generate an electrical signal corresponding to an amount of acetone contained in the exhaled gas existing inside the sample gas chamber; and a heater configured to increase a temperature of the internal space of the sample gas chamber to prevent moisture contained in the exhaled gas from being condensed in the sample gas chamber.

The sample gas passage includes an inlet, an outlet, a sample gas collection port formed between the inset and the outlet of the sample gas passage to communicate with the sample gas chamber, and a protrusion formed between the inlet of the sample gas passage and the sample gas collection port so as to extend radially inward from an inner surface of the sample gas passage to reduce an inner diameter of a section of the sample gas passage. A pressure sensor is installed between the inlet and the protrusion of the sample gas passage.

The device may further include: a pump installed between the sample gas passage and the sample gas chamber and configured to, when operated, introduce the exhaled gas flowing through the sample gas passage into the sample gas chamber and, when stopped, close the inlet of the sample gas chamber.

The device may further include: a valve connected to the outlet of the sample gas chamber.

The valve may be a one-way valve.

The device may further include: a signal processing unit configured to control the pump and the valve. The signal processing unit may control the pump and the valve so that the valve is opened during an operation of the pump and closed during stoppage of the pump.

The signal processing unit may control the photoionization detector so as to operate in a state in which the pump is stopped, the valve is closed, and the exhaled gas to be measured is filled in the sample gas chamber.

The device may further include: a sensor capable of detecting an increase or decrease of a flow rate of the exhaled gas flowing through the sample gas passage.

The sample gas passage may be formed in a cylindrical shape so as to have a constant inner diameter.

The device may further include: a sensor capable of detecting an increase or decrease of a flow rate of the exhaled gas flowing through the sample gas passage; and a signal processing unit configured to, based on a signal regarding the increase or decrease of the flow rate of the exhaled gas received from the sensor, transmit a control signal to the pump so that the pump is operated at a timing at which a final exhaled gas flows through the sample gas passage.

The outlet of the sample gas passage has an inner diameter larger than an inner diameter of a section of the sample gas passage reduced by a protrusion.

The body fat combustion amount measurement device according to the present invention can measure a body fat combustion amount in real time. The measurement time is as short as a few seconds. Therefore, the body fat combustion amount measurement device can inform a user, who performs a diet and exercise for the purpose of weight loss, of body fat combustion in real time.

DETAILED DESCRIPTION

Figure 1:
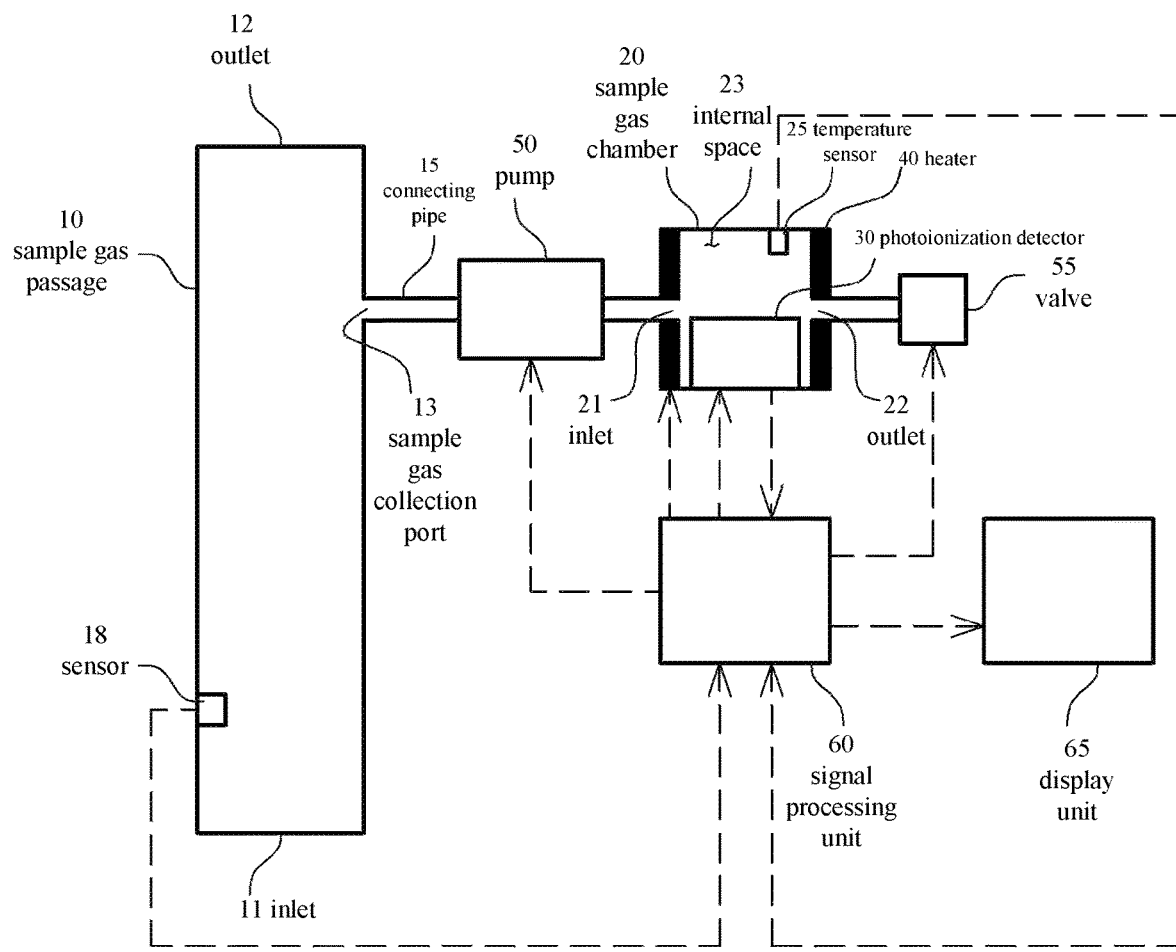
FIG. 1 is a configuration diagram of a body fat combustion amount measurement device according to an embodiment of the present invention.

Hereinafter, a preferred embodiment of the present invention will be described in detail with reference to the accompanying drawings. The following embodiment is provided as an example to ensure that the spirit of the present invention is sufficiently conveyed to those skilled in the art. Therefore, the present invention is not limited to the embodiment described below and may be embodied in other forms. In the drawings, the width, length, thickness and the like of components may be exaggerated for the sake of convenience. The same components are denoted by like reference numerals throughout the specification.

FIG. 1 is a configuration diagram of a body fat combustion amount measurement device according to an embodiment of the present invention. Referring to FIG. 1, the body fat combustion amount measurement device 1 includes a sample gas passage 10 through which an exhaled gas flows, a sample gas chamber 20 into which a part of the exhaled gas flowing through the sample gas passage 10 is introduced, a photoionization detector 30 disposed in an internal space of the sample gas chamber 20, a heater 40 configured to raise a temperature of the internal space of the sample gas chamber 20, and a pump 50 configured to supply the exhaled gas flowing through the sample gas passage 10 to the sample gas chamber 20.

The sample gas passage 10 is a passage through which the exhaled gas blown by a user (a subject) passes. The exhaled gas may be blown into the sample gas passage 10 through a blowing tube (not shown) which is attachable to or detachable from the sample gas passage 10, or may be directly blown into the sample gas passage 10.

The sample gas passage 10 preferably has a cylindrical shape having a constant internal diameter over the entire portion including an inlet 11 and an outlet 12 thereof. This is because if the diameter of the outlet side portion of the sample gas passage 10 is smaller than the diameter of the inlet side portion as in a conventional gas concentration measurement device, the pressure inside the sample gas passage 10 increases such that the moisture in the exhaled gas is highly likely to undergo dew condensation in the sample gas passage 10. This is because if the pressure inside the sample gas passage 10 is high, the water vapor in the exhaled gas is easily saturated and thus the dew point temperature is further increased. When the moisture of the exhaled gas enters the sample gas chamber 20, the photoionization detector 30 is contaminated, which makes it difficult to accurately measure the amount of acetone contained in the exhaled gas. On the contrary, when the diameter of the outlet 12 is larger than the diameter of the inlet 11, the ambient air may be introduced through the outlet 12 of the sample gas passage 10.

In addition, if the sample gas passage 10 has a structure that obstructs the flow of the exhaled gas, the pressure applied to the sample gas passage 10 may be largely changed by the difference in the intensity at which the exhaled gas is blown into the sample gas passage 10 by the subject. When the pressure applied to the sample gas passage 10 is changed, the pressure of the exhaled gas flowing into the photoionization detector 30 may also be changed. In general, the photoionization detector 30 reacts sensitively to the pressure of the gas to be measured. Therefore, the change in the pressure applied to the sample gas passage 10 may prevent accurate measurement. Accordingly, it is preferable for the sample gas passage 10 to have a structure not applied with a high pressure in order to minimize the difference in the pressure applied to the sample gas passage 10, which varies depending on the intensity at which the exhaled gas is blown into the sample gas passage 10 by the subject.

A sample gas collection port 13 for collecting a part of the exhaled gas is formed between the outlet 12 and the inlet 11 of the sample gas passage 10. A part of the exhaled gas flowing through the sample gas passage 10 is supplied to the sample gas chamber 20 through the sample gas collection port 13.

The sample gas chamber 20 includes an inlet 21 through which the exhaled gas passing through the sample gas collection port 13 of the sample gas passage 10 is introduced and an outlet 22 through which the introduced exhaled gas is discharged. The sample gas chamber 20 defines an internal space 23 in which the introduced exhaled gas flows. The sample gas chamber 20 may be made of a metallic material having high thermal conductivity, such as copper or copper alloy. The sample gas chamber 20 serves to isolate the photoionization detector 30, the pump 50 and the valve 55 from the external environment so that they are placed in an appropriate measurement environment.

The photoionization detector 30 is disposed in the internal space 23 of the sample gas chamber 20. The photoionization detector 30 has an advantage in that it enjoys high accuracy and sensitivity and has a small size.

The photoionization detector 30 utilizes the fact that when a gas is irradiated with light such as ultraviolet light or the like having higher energy than the ionization energy of a gas to be detected, the gas is ionized and the degree of ionization of the gas is outputted in the form of ion current. The concentration of the gas to be measured is determined by the magnitude of the ion current. In the present invention, the content of an acetone component is measured by irradiating the exhaled gas with ultraviolet rays to ionize the acetone component to be measured and measuring an ion current using an electrode. However, if moisture enters the inside of the sample gas chamber 20 or if water vapor contained in the exhaled gas is condensed inside the sample gas chamber 20, the ion current value of the photoionization detector 30 decreases sharply, which makes it difficult to perform measurement. This is because the moisture covers a portion of a window of an ultraviolet lamp to absorb ultraviolet light, or covers a portion of an electrode so that ions cannot reach the surface of the electrode.

The heater 40 keeps the temperature of the sample gas chamber 20 higher than the dew point temperature of the exhaled gas to prevent condensation of moisture in the sample gas chamber 20. The heater 40 may be, for example, a film heater surrounding the sample gas chamber 20. The heater 40 may maintain the temperature of the sample gas chamber 20 at a temperature higher than the human body temperature, for example, about 40 degrees C. A temperature sensor 25 capable of measuring the temperature inside the sample gas chamber 20 may be provided in the sample gas chamber 20.

The pump 50 is installed between the sample gas passage 10 and the sample gas chamber 20. That is, the pump 50 is installed in a connecting pipe 15 that connects the sample gas collection port 13 of the sample gas passage 10 and the inlet 21 of the sample gas chamber 20. When the pump 50 is operated, a quantity of exhaled gas is introduced into the sample gas chamber 20 through the inlet 21 of the sample gas chamber 20. Since the pump 50 is installed between the sample gas passage 10 and the sample gas chamber 20, a part of the exhaled gas is supplied to the sample gas chamber 20 in such a way that the exhaled gas is blown into the inside of the sample gas chamber 20 during the operation of the pump 50. Therefore, a positive pressure is applied to the sample gas chamber 20. If the positive pressure is applied to the sample gas chamber 20, the measurement sensitivity of the photoionization detector 30 is improved. When the operation of the pump 50 is stopped, the pump 50 serves to seal the inlet 21 of the sample gas chamber 20.

A sensor 18 capable of detecting the increase or decrease of the flow rate of the exhaled gas may be installed in the sample gas passage 10. Examples of such a sensor 18 include a flow sensor, a pressure sensor, a microphone, and the like. The sensor 18 is used to determine the timing of collection of the exhaled gas. The exhaled gas contains not only acetone but also other components such as $H_2S$ or organic sulfur compounds that can be detected by the photoionization detector 30. By the way, acetone in the exhaled gas is generated due to the gas exchange between the air of the alveoli and the capillaries that occur in the lungs. Therefore, acetone is mainly contained in the final exhaled gas, which is the last part of the exhaled gas. Accordingly, collecting the final exhaled gas is advantageous for accurate measurement of a body fat combustion amount. If the sensor 18 capable of detecting the increase or decrease of the flow rate of the exhaled gas is used, it is possible to detect the timing at which the flow rate decreases. This makes it possible to know the timing at which the final exhaled gas is introduced.

Figure 2:
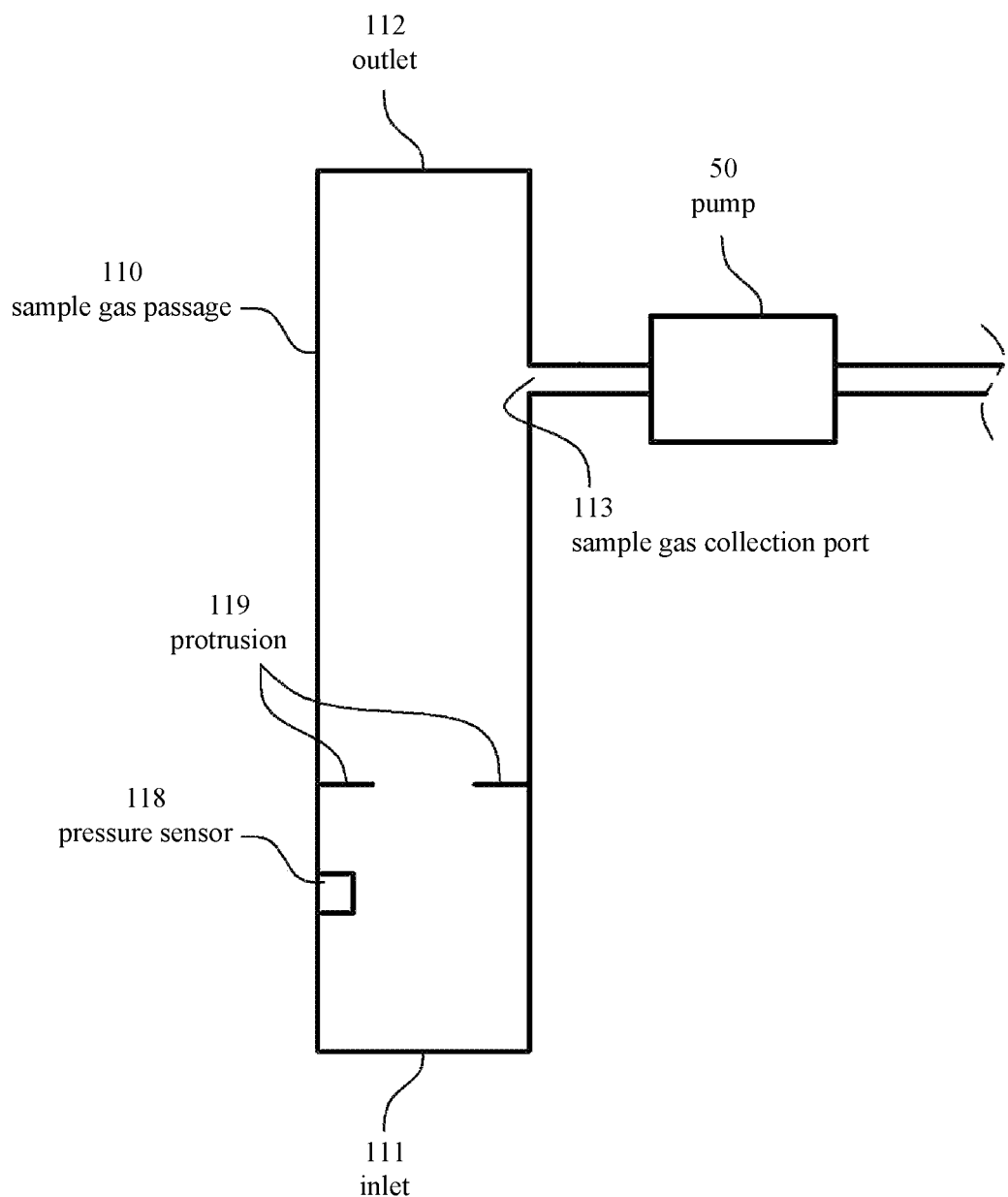
FIG. 2 is a partial configuration diagram of a body fat combustion amount measurement device according to another embodiment of the present invention.

FIG. 2 is a partial configuration diagram of a body fat combustion amount measurement device according to another embodiment of the present invention. FIG. 2 illustrates a case where a pressure sensor 118 is installed in a sample gas passage 110. A protrusion 119 extending radially inward from the inner surface of the sample gas passage 110 to reduce the inner diameter of a certain section of the sample gas passage 110 is formed at the rear end of the pressure sensor 118 installed on the side of the inlet 111. The protrusion 119 serves to enable the pressure sensor 118 to easily capture a change in the pressure inside the sample gas passage 110. As described above, in order to minimize the influence of moisture condensation due to the increase in the pressure inside the sample gas passage 110 and the change in the pressure of the exhaled gas introduced into the sample gas chamber, the pressure sensor 118 and the protrusion 119 are disposed on the side of the inlet 111 far from the sample gas collection port 113. The inner diameter of the outlet 112 is preferably equal to or greater than the inner diameter of the section in which the protrusion 119 is formed.

Referring back to FIG. 1, the body fat combustion amount measurement device 1 may further include a valve 55. The valve 55 is provided on the side of the outlet 22 of the sample gas chamber 20. The valve 55 is installed in order to prevent the ambient air other than the exhaled gas from entering the sample gas chamber 20. The valve 55 may be a one-way valve capable of discharging only the sample gas existing in the sample gas chamber 20. Alternatively, the valve 55 may be a solenoid valve synchronized with the pump 50.

Furthermore, the body fat combustion amount measurement device 1 includes a signal processing unit 60 and a display unit 65. The signal processing unit 60 may process the electrical signal received from the photoionization detector 30 to calculate the body fat combustion amount of the subject. In addition, the signal processing unit 60 controls the heater 40 based on the temperature value received from the temperature sensor 25. Moreover, the signal processing unit 60 may control the operation timings of the pump 50 and the solenoid valve using the signal of the sensor 18 capable of detecting the increase or decrease of the flow rate of the sample gas, so that the final exhaled gas can be introduced into the sample gas chamber 20. In addition, the operation timing of the photoionization detector 30 may be controlled using the signal of the sensor 18.

The display unit 65 displays the body fat combustion amount calculated by the signal processing unit 60. When the sample gas is not sufficiently supplied, the display unit 65 may notify the subject through lighting or an alarm that the sample gas is not sufficiently supplied.

Hereinafter, the operation of the body fat combustion amount measurement device 1 according to an embodiment of the present invention will be described.

The body fat combustion amount is measured by a method of comparing the amount of acetone contained in the exhaled gas before exercise with the amount of acetone contained in the exhaled gas after exercise. There is an individual difference in the amount of acetone contained in the exhaled gas. For example, a diabetic has a significant amount of acetone contained in an exhaled gas even before exercise. Therefore, the body fat combustion amount is measured based on the difference between the amount of acetone before exercise and the amount of acetone after exercise instead of the absolute amount of acetone after exercise.

When a start button (not shown) on the surface of the body fat combustion amount measurement device 1 is pressed, a current is applied to the heater 40, whereby the sample gas chamber 20 is heated. When the temperature value measured by the temperature sensor 25 is equal to or greater than a predetermined reference value, it is displayed on the display unit 65 that the measurement preparation is completed.

When the subject injects the exhaled gas into the body fat combustion amount measurement device 1 through a blowing tube before starting exercise, the exhaled gas is introduced into the sample gas passage 10. When it is confirmed by the pressure sensor or the like that the flow rate of the exhaled gas increases and then decreases, the solenoid valve is opened at the flow rate decreasing timing, and the pump 50 is operated momentarily so that the final exhaled gas is introduced into the sample gas chamber 20 through the inlet 21 and the gas filled in the sample gas chamber 20 is discharged. When the final exhaled gas is introduced into the sample gas chamber 20, the valve 55 is closed and the pump 50 is stopped to close both the inlet 21 and the outlet 22 of the sample gas chamber 20. The photoionization detector 30 generates an electrical signal according to the amount of acetone contained in the introduced final exhaled gas. This electrical signal is transmitted to the signal processing unit 60 and stored as a reference value. In order to increase the lifespan of the photoionization detector 30, it is preferable to operate the photoionization detector 30 only when measuring the amount of acetone. That is, it is preferable to operate the photoionization detector 30 after the exhaled gas to be measured is introduced into the sample gas chamber 20 and then the inlet 21 and the outlet 22 are closed.

When the measurement is completed, the valve 55 remains closed until the next measurement. In the case of using a one-way valve, there is an advantage in that the valve 55 does not have to be controlled separately.

Next, the amount of acetone contained in the final exhaled gas is measured in the same manner during or after the exercise of the subject. The signal processing unit 60 first calculates a body fat combustion amount of a subject based on the difference between the reference value measured before exercise and the amount of acetone and then transmits the body fat combustion amount to the display unit 65. The display unit 65 displays the body fat combustion amount thus transmitted.

The embodiments described above are presented to merely describe preferred embodiments of the present invention. The scope of the present invention is not limited to the above-described embodiments. Those skilled in the art may make various changes, modifications or substitutions within the spirit of the present invention and the claims. It is to be understood that such changes, modifications or substitutions fall within the scope of the present invention.

What is claimed is:

1. A body fat combustion amount measurement device, comprising: a sample gas passage through which an exhaled gas flows; a sample gas chamber having an inlet through which a part of the exhaled gas flowing through the sample gas passage is introduced and an outlet through which the exhaled gas is discharged, the sample gas chamber configured to define an internal space through which the exhaled gas flows; a photoionization detector disposed in the internal space of the sample gas chamber and configured to generate an electrical signal corresponding to an amount of acetone contained in the exhaled gas existing inside the sample gas chamber; and a heater configured to increase a temperature of the internal space of the sample gas chamber to prevent moisture contained in the exhaled gas from being condensed in the sample gas chamber, wherein the sample gas passage includes an inlet, an outlet, a sample gas collection port formed between the inlet and the outlet of the sample gas passage to communicate with the sample gas chamber, and a protrusion formed between the inlet of the sample gas passage and the sample gas collection port so as to extend radially inward from an inner surface of the sample gas passage to reduce an inner diameter of a section of the sample gas passage, and a pressure sensor is installed between the inlet and the protrusion of the sample gas passage.

2. The device according to claim 1, further comprising:
a pump installed between the sample gas passage and the sample gas chamber and configured to, when operated, introduce the exhaled gas flowing through the sample gas passage into the sample gas chamber and, when stopped, close the inlet of the sample gas chamber.

3. The device according to claim 2, further comprising:
a valve connected to the outlet of the sample gas chamber.

4. The device according to claim 3, wherein the valve is a one-way valve.

5. The device according to claim 3, further comprising:
a signal processing unit configured to control the pump and the valve,
wherein the signal processing unit controls the pump and the valve so that the valve is opened during an operation of the pump and closed during stoppage of the pump.

6. The device according to claim 5, wherein the signal processing unit controls the photoionization detector so as to operate in a state in which the pump is stopped, the valve is closed, and the exhaled gas to be measured is filled in the sample gas chamber.

7. The device according to claim 2, further comprising:
a sensor capable of detecting an increase or decrease of a flow rate of the exhaled gas flowing through the sample gas passage.

8. The device according to claim 2, wherein the sample gas passage is formed in a cylindrical shape so as to have a constant inner diameter.

9. The device according to claim 2, further comprising:
a sensor capable of detecting an increase or decrease of a flow rate of the exhaled gas flowing through the sample gas passage; and
a signal processing unit configured to, based on a signal regarding the increase or decrease of the flow rate of the exhaled gas received from the sensor, transmit a control signal to the pump so that the pump is operated at a timing at which a final exhaled gas flows through the sample gas passage.

10. The device according to claim 1, wherein the outlet of the sample gas passage has an inner diameter larger than an inner diameter of a section of the sample gas passage reduced by a protrusion.

* * * * *